United States Patent [19]
Styczynski et al.

[11] Patent Number: 6,037,326
[45] Date of Patent: *Mar. 14, 2000

[54] REDUCTION OF HAIR GROWTH

[76] Inventors: Peter Styczynski, P.O. Box 387, Mount Airy, Md. 21771; Gurpreet S. Ahluwalia, 8632 Stableview Ct., Gaithersburg, Md. 20852

[*] Notice: This patent issued on a continued prosecution application filed under 37 CFR 1.53(d), and is subject to the twenty year patent term provisions of 35 U.S.C. 154(a)(2).

[21] Appl. No.: 08/777,803

[22] Filed: Dec. 31, 1996

[51] Int. Cl.$^7$ .............................. A61K 31/70; A61K 7/06
[52] U.S. Cl. ............................. 514/23; 424/70.1; 514/25; 514/183; 514/187; 514/297; 514/451; 514/453; 514/457; 514/880
[58] Field of Search ................................ 514/23, 25, 183, 514/187, 297, 451, 453, 457, 880; 424/70.1

[56] References Cited

U.S. PATENT DOCUMENTS

| | | | |
|---|---|---|---|
| 3,426,137 | 2/1969 | Philpitt et al. | 424/330 |
| 4,039,669 | 8/1977 | Beyler et al. | 424/243 |
| 4,139,638 | 2/1979 | Neri et al. | 424/324 |
| 4,161,540 | 7/1979 | Neri et al. | 424/324 |
| 4,191,775 | 3/1980 | Glea | 424/304 |
| 4,269,831 | 5/1981 | Ferrari et al. | 424/241 |
| 4,370,315 | 1/1983 | Greff et al. | 424/94 |
| 4,439,432 | 3/1984 | Peat | 424/240 |
| 4,508,714 | 4/1985 | Cecic et al. | 424/195.1 |
| 4,517,175 | 5/1985 | Iwabuchi et al. | 424/70 |

(List continued on next page.)

FOREIGN PATENT DOCUMENTS

| | | |
|---|---|---|
| 0413528A1 | 10/1990 | European Pat. Off. . |
| 0532219A2 | 2/1992 | European Pat. Off. . |
| 0 591 583 A1 | 4/1994 | European Pat. Off. . |
| 0 703 221 A1 | 3/1996 | European Pat. Off. . |
| 8217640 | 8/1996 | Japan . |
| 1 458 349 | 12/1976 | United Kingdom . |
| WO 95/05821 | 3/1995 | WIPO . |
| WO 97/42964 | 11/1997 | WIPO . |
| WO 97/44321 | 11/1997 | WIPO . |

OTHER PUBLICATIONS

Poot, "Impaired S–Phase Transit of Werner Syndrome Cells Expressed in Lymphoblastoid Cell Lines," Experimental Cell Research 202:267–273 (1992).

PCT International Search Report for PCT/US 97/24268, mailed May 26, 1998.

Pegg et al. *Fundam. Appl. Toxicol.*, vol. 32(1): 45–52, (1996) (Abstract Only).

Berger et al., Nature, Structure and mechanism of DNA topoisomerase II, 225–32 1996.

Oh et al., Proc. Natl. Acad. Sci. USA, "An estrogen receptor pathway regulates the telogen–anagen hair follicle transition and influences epidermal cell proliferation", 12525–30, 1996.

Benchokroun et al., Biochemical Pharmacology, "Aurintricarboxylic Acid, A Putative Inhibitor of Apoptosis is a Potent Inhibitor of DNA Topoisomerase II In Vitro and in Chinese Hamster Fibrosarcoma Cells", 305–13, 1995.

Constantinou et al., Journal of Natural Products, "Flavonoids as DNA Topoisomerase Antagonists and Poisons: Structure–Activity Relationships", 217–25, 1995.

Harmon et al., British Journal of Dermatology, "Hair Fibre Production by Human Hair Follicles in Whole–organ Culture," 415–423, 1994.

Harmon et al., SID Abstracts, "12–O–Tetradecanoylphorbol–12–Acetate Inhibits Human Hair Follicle Growth and Hair Fiber Production in Whole–organ Cultures," 102:533 1994.

Philpott et al., Journal of Dermatological Science, "Human Hair Growth in vitro: A Model for the Study of Hair Follicle Biology," 7:S55–S72, 1994.

(List continued on next page.)

*Primary Examiner*—Howard C. Lee
*Attorney, Agent, or Firm*—Fish & Richardson P.C.

[57] ABSTRACT

Mammalian hair growth is reduced by applying to the skin an inhibitor of a DNA topoisomerase.

55 Claims, 1 Drawing Sheet

TABLE II

Inhibition of Flank Organ Hair Follicle DNA Topoisomerase In Vitro

| Compound | Concentration (mM) | % Inhibition |
|---|---|---|
| etoposide | 1.25 | 29 |
| nalidixic acid | 1 | 66 |
| novobiocin | 2.5 | 92 |

U.S. PATENT DOCUMENTS

| | | | |
|---|---|---|---|
| 4,720,489 | 1/1988 | Shander | 514/171 |
| 4,885,289 | 12/1989 | Brener et al. | 514/170 |
| 4,935,231 | 6/1990 | Pigiet | 424/71 |
| 5,095,007 | 3/1992 | Ahluwalia | 514/23 |
| 5,096,911 | 3/1992 | Ahluwalia et al. | 514/380 |
| 5,132,293 | 7/1992 | Shander et al. | 514/46 |
| 5,143,925 | 9/1992 | Shander et al. | 514/378 |
| 5,189,212 | 2/1993 | Ruenitz | 562/468 |
| 5,271,942 | 12/1993 | Heverhagen | 424/451 |
| 5,300,284 | 4/1994 | Wiechers et al. | 424/70 |
| 5,364,885 | 11/1994 | Ahluwalia et al. | 514/563 |
| 5,411,991 | 5/1995 | Shander et al. | 514/665 |
| 5,455,234 | 10/1995 | Ahluwalia et al. | 514/46 |
| 5,474,763 | 12/1995 | Shander et al. | 424/73 |
| 5,554,608 | 9/1996 | Ahluwalia et al. | 514/212 |

OTHER PUBLICATIONS

Gorbsky, Cancer Research, Cell Cycle Progression and Chromosome Segregation in Mammalian Cells Cultured in the Presence of the Topoisomerase II Inhibitors ICRF–187 . . . , 1042–48, 1994.

Wang, Advances in Pharmacology, "DNA Topoisomerases as Targets of Therapeutics: An Overview", 1–19, 1994.

Mizumoto et al., Molecular Pharmacology, Programmed Cell Death (Apoptosis) of Mouse Fibroblasts is Induced by the Topoisomerase II Inhibitor Etposide, 890–95, 1994.

Barrows et al., Makaluvamines, marine natural products, are actve anti–cancer agents and DNA topo II inhibitors, 333–347, 1993.

Jindo et al., The Journal of Dermatology, "Organ Culture of Mouse Vibrissal Hair Follicles in Serum–free Medium," 20:756–762, 1993.

Messenger, The Society for Investigative Dermatology, "The Control of Hair Growth: An Overview," 1011:4S–9S, 1993.

Li et al., Proc. Natl. Acad. Sci. USA, "Hair Shaft Elongation, Follicle Growth, and Spontaneous Regression in Long–term, Gelatin Sponge–supported Histoculture of Human Scalp Skin," 89:8764–8768, 1992.

Li et al., In Vitro Cell. Dev. Biol., "Skin Histoculture Assay for Studying the Hair Cycle," 28A:695–698, 1992.

Yanabe et al., Cancer Research, Inhibition of Topoisomerase II by Antitumor Agents Bis(2,6–dioxopiperazine) Derivatives, 4903–08, 1991.

Salzer et al., Pharmacology Hear. Res. "Cochlear Damage and Increased Threshold in Alpha–difluoromethylornithine DFMO Treated Guinea Pigs," 451–2:101–112, 1990 Abstract.

Drake et al., Cancer Research, In Vitro and Intracellular Inhibition of Topoisomerase II by the Antitumor Agent Merbarone, 2578–83, 1989.

Adlakha et al., Cancer Research, Modulation of 4'–(9–Acridinylamino)methanesulfon–m–anisidide–induced, Topoisomerase II–mediated DNA Cleavage by Gossypol, 2052–48, 1989.

Drlica et al., American Chemical Society, "Inhibitors of DNA Topoisomerases", 2253–59, 1988.

Heck et al., Proc. Natl. Acad. Society, Differential expression of DNA topoisomerases I and II during the eukaryotic cell cycle, 1086–90, 1988.

Goos et al., Arch. Dermatol. Res., "An Improved Method for Evaluating Antiandrogens," 273:333–341, 1982.

Johnson et al., Biochemistry, "Inhibition of Hexokinase and Protein Kinase Activities of Tumor Cells by a Chloromethyl Ketone Derivative of Lactic Acid," 2122:2984–2989, 1982.

Marini et al., The Journal of Biological Chemistry, "Decantentation of Kinetoplast DNA by Topoisomerases", 4976–79, 1980.

Simpson et al., British Journal of Dermatology, "The Effect of Topically Applied Progesterone on Sebum Excretion Rate," 100:687–692, 1979.

Sato, Biology and Disease of the Hair, "The Hair Cycle and its Control Mechanism," 3–13, 1976.

Adachi et al., J. Soc. Cosmet. Chem., "Human Hair Follicles: Metabolism and Control Mechanisms," 21:901–924, 1970.

TABLE II

Inhibition of Flank Organ Hair Follicle DNA Topoisomerase In Vitro

| Compound | Concentration (mM) | % Inhibition |
|---|---|---|
| etoposide | 1.25 | 29 |
| nalidixic acid | 1 | 66 |
| novobiocin | 2.5 | 92 |

REDUCTION OF HAIR GROWTH

The invention relates to reducing hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic anti-androgens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

DNA topoisomerase are a family of enzymes that are involved in DNA replication and metabolism. The enzymes tie or untie DNA knots so that the DNA can replicate effectively. They regulate the helical structure of the double-stranded DNA by breaking one (topoisomerase type I) or both (topoisomerase type II) strands of the DNA helix (See Wang J. Adv. Pharmacol. 29A:1–19, 1994). Topoisomerase I appears to sense and relieve the torsional pressure that accumulates during DNA transcription. Topoisomerase II is involved in the separation of intertwined DNA strands.

DNA topoisomerase types I and II can be inhibited by direct interaction at the catalytic or active site of the protein. In addition, DNA topoisomerase type II is dependent upon ATP and requires the formation of an intermediate complex with the DNA substrate. Therefore, prevention of ATP binding or stabilization of the intermediate enzyme-DNA complex are known mechanisms of topoisomerase inhibition.

It has now been found that unwanted mammalian (including human) hair growth—particularly androgen-stimulated hair growth—can be reduced by applying to the skin a composition including an inhibitor of a DNA topoisomerase, e.g., DNA topoisomerase I or DNA topoisomerase II, in an amount effective to reduce hair growth. The unwanted hair growth which is reduced may be normal hair growth, or hair growth that results from an abnormal or diseased condition.

Classes of topoisomerase inhibitors include coumarins, quinolones, epipodophyllotoxins, flavanoids, and actinomycins.

Specific inhibitors include novobiocin and nalidixic acid (Drlica, K. and Franco, R., J. Biochem. 27:2253–2259, 1988); etoposide (Mizumoto et al., Mol. Pharm. 46:860–895, 1994); ellagic acid (Constantinou et al., Nutrition and Cancer 23:121–130, 1995); bisbenzamide (or Hoechst 33342) (Sumner, A. T. Exp. Cell. Res. 217:440–447, 1995); bufalin (Jap J. Cancer Res. 85:645–651, 1994); terpentecin (J. Antiobiot. 48:211–216, 1995); bisdioxopiperizine analogs such as dexrazoxane (ICRF-187) and razoxane (ICRF-159) (Hasinoff et al., Biochem. Pharmacol. 50:953–958, 1995); 1,2-bis(3,5-dioxopiperazinyl-1-yl)propane (Gorbsky, G., Cancer Res. 54:1042–1048, 1994); 1,2,3,4-tetrahdyro-β-carboline derivatives (Lehnert et al., 4:2411–2416, 1994); pyridoacridine alkaloids such as dehydrokuanoniamine B and shermilamine C (McDonald et al., J. Med Chem. 37:3819–3827, 1994); azatoxin (Solary et al., Biochem. Pharmacol. 45:2449–2456, 1993); 2-.hydroxy-3,8,9-trimethoxy-5-methylbenzo[c]phenanthridine also known as fagaronine (Larsen et al. Biochem. Pharmacol. 46:1403–1412, 1993); 4-hydroxymethyl-4',5'-benzopsoralen (Mutation Res.: Fund. Mol. Mech. Mut. 311:277–285, 1994); saintopin (J. Biol. Chem. 269:28702–28707, 1994); makaluvamines, isolated from a sponge of the genus Zyzzya (Barrows et al., Anti-Cancer Drug Des. 8:333–347, 1993); acridines, such as amsacrine (Nelson et al., Proc. Natl. Acad. Sci. 81:1361–1365, 1984); ellipticines (Pommier et al., Biochem. 24:6410–6416, 1985); amonafide (Corbett, A. H. and Osheroff, N., Chem. Res. Toxicol. 6:585–597, 1993); epipodophyllotoxins (Ross et al., Cancer Res. 44:5857–5860, 1984); anthracenediones (De Isabella et al., Mol. Pharmacol. 43:715–721, 1993); merbarone and teniposide (Chen, M and Beck, W. T., Cancer Res. 55:1509–1516, 1995); indole-4,7-quinones (J. Org. Chem. 60:3543–3545, 1995); elenic acid (Juagdan et al. Tetrahedron Lett. 36:2905–2908, 1995); 1-cyclopropyl-6,8-difluro-1,4-dihydro-7-(2,6-dimethyl-4-pyridinyl)-4-substituted quinolines (Kuo et al., Bioorg. Med. Chem. Lett. 5:399–404, 1995); and 3-benzylquinolines (Eissenstat et al., Bioorg. Med. Chem. Lett. 5:1021–1026, 1995).

The inhibitors of a DNA topoisomerase preferably are incorporated in a topical composition which preferably includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US93/0506A. In addition, a penetration enhancer may be added to the vehicle to further enhance the effectiveness of the formulation.

The concentration of the inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. The effective amounts may range, for example, from 10 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency of hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a composition including an inhibitor of a DNA topoisomerase, the flank organs of each of a group of hamsters are depilated by applying a thioglycolate based chemical depilatory (Surgex) and/or shaved. To one organ of each animal 10 $\mu$l. of vehicle alone once a day is applied, while to the other organ of each animal an equal amount of vehicle containing an inhibitor of a DNA topoisomerase is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 30%, more preferably at least about 50%, and most preferably at least about 60% when tested in the Golden Syrian hamster assay. A number of known inhibitors of DNA topoisomerase were tested in the Golden Syrian hamster assay; the results are provided in Table 1:

TABLE I

Effect of Topoisomerase Inhibitors on Hair Mass

| Compounds | Vehicle | [b]pH | Dose | % Reduction | Hair Mass (mg) Treated | Vehicle Control |
|---|---|---|---|---|---|---|
| novobiocin | A | 8.0 | 10% | 75 ± 6 | 0.67 ± .17 | 2.90 ± .42 |
| nalidixic acid | B | 5.5 | 10% | 63 ± 6 | 0.67 ± .05 | 1.93 ± .58 |
| etoposide | C | 6.0 | 10% | 60 ± 6 | 0.96 ± .17 | 2.19 ± .58 |
| ellagic acid[a] | D | | 20% | 39 ± 10 | 1.13 ± .10 | 2.14 ± .33 |
| kaempferol | E | 4.5 | 10% | 75 ± 5 | 0.50 ± .12 | 1.92 ± .26 |
| gossypol | C | 4.0 | 10% | 59 ± 6 | 0.50 ± .12 | 1.31 ± .26 |
| morina | E | 4.5 | 7.5% | 48 ± 6 | 0.74 ± .11 | 2.50 ± .47 |
| bis-benzamide[a] | A | 4.0 | 10% | 58 ± 5 | 1.33 ± .14 | 3.18 ± .18 |

[a]Type I and type II inhibitor;
[b]vehicle A = water (68%), ethanol (16%), propylene glycol (5%), dipropylene glycol (5%), benzyl alcohol (4%) and propylene carbonate (2%); Vehicle B = ethanol (70%), propylene glycol (30%); Vehicle C = dimethyl sulfoxide (50%), ethanol (35%), dipropylene glycol (15%); Vehicle D = water 80.84%), glyceryl stearate SE (4.24%), polyethylene glycol stearate (4.09%), cetearyl alcohol (3.05%), ceteareth-20 (2.5%), mineral oil (2.22%), stearyl alcohol (1.67%) and dimethicone (0.56%); Vehicle E = acetone (40%), ethanol (30%), dipropylene glycol (30%).

Hair follicle extracts from hamsters flank organs were used as a topoisomerase source for in vitro experiments that demonstrate the presence of topoisomerase II in flank organ hair follicles, and that the inhibition of topoisomerase II by inhibitors tested in the Golden Syrian hamster assay using a kit supplied by TopoGen, Inc., Columbus, Ohio. The assay measures the decatenation of catenated DNA (kDNA) following incubation at 37° C. with flank organ-derived hair follicle extract and the appropriate buffer containing $MgCl_2$ and ATP. Inhibitors of a DNA topoisomerase were tested at concentrations listed in Table II, FIG. 1. The reaction mixture is analyzed by agarose gel electrophoresis, and the migration pattern of the decatenated DNA is determined using standards provided in the kit. Relative quantitation of decatenated DNA bands representing topoisomerase II catalytic activity was performed by scanning a polaroid photograph of the gel followed by subsequent computer-assisted analysis using Adobe Photoship (Adobe Systems, Inc., Mountain View, Calif.) and IPGEL Lab (Signal Analytics, Vienna, Va.) software packages.

DETAILED DESCRIPTION OF THE DRAWINGS

Figure 1:
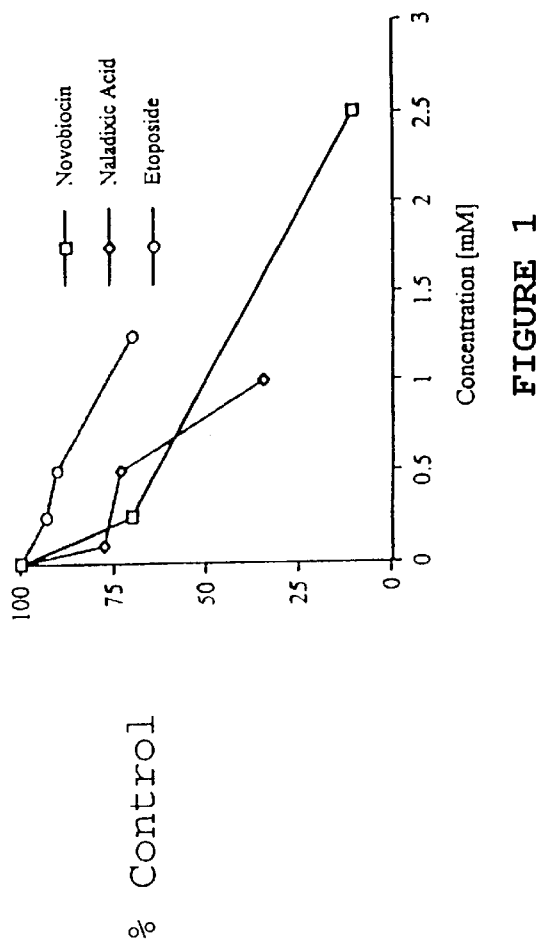

FIG. 1. Dose-dependent inhibition of flank organ topoisomerase II activity.

Both in-vitro and in-vivo studies suggest that inhibition of DNA topoisomerase, particularly type II, is a mechanism for reducing the growth of hair.

Other embodiments are within the claims.

We claim:

1. A method of reducing mammalian hair growth which comprises
    selecting an area of skin from which reduced hair growth is desired; and
    applying to said area of skin a dermatologically acceptable composition comprising an inhibitor of a DNA topoisomerase in an amount effective to reduce hair growth.

2. The method of claim 1, wherein said inhibitor comprises a coumarin.

3. The method of claim 1, wherein said inhibitor comprises a quinolone.

4. The method of claim 1, wherein said inhibitor comprises a epipodophyllotoxin.

5. The method of claim 1, wherein said inhibitor comprises a actinomycin.

6. The method of claim 1, wherein said inhibitor comprises novobiocin.

7. The method of claim 1, wherein said inhibitor comprises nalidixic acid.

8. The method of claim 1, wherein said inhibitor comprises etoposide.

9. The method of claim 1, wherein said inhibitor comprises ellagic acid.

10. The method of claim 1, wherein said inhibitor comprises bisbenzamide.

11. The method of claim 1, wherein said inhibitor comprises bufalin.

12. The method of claim 1, wherein said inhibitor comprises terpentecin.

13. The method of claim 1, wherein said inhibitor comprises a bisdioxopiperizine analog.

14. The method of claim 13, wherein said inhibitor comprises dexrazoxane.

15. The method of claim 13, wherein said inhibitor comprises razoxane.

16. The method of claim 1, wherein said inhibitor comprises 1,2-bis(3,5-dioxopiperazinyl-1-yl)propane.

17. The method of claim 1, wherein said inhibitor comprises a 1,2,3,4-tetrahydro-$\beta$-carboline derivative.

18. The method of claim 1, wherein said inhibitor comprises a pyridoacridine alkaloid.

19. The method of claim 18, wherein said inhibitor comprises a dehydrokuanoniamine B.

20. The method of claim 18, wherein said inhibitor comprises a shermilamine C.

21. The method of claim 1, wherein said inhibitor comprises azatoxin.

22. The method of claim 1, wherein said inhibitor comprises agaronine.

23. The method of claim 1, wherein said inhibitor comprises 4-hydroxymethyl-4', 5'-benzopsoralen.

24. The method of claim 1, wherein said inhibitor comprises saintopin.

25. The method of claim 1, wherein said inhibitor comprises a makaluvamine.

26. The method of claim 1, wherein said inhibitor comprises an acridine.

27. The method of claim 26, wherein said inhibitor comprises amsacrine.

28. The method of claim 1, wherein said inhibitor comprises an ellipticine.

29. The method of claim 1, wherein said inhibitor comprises amonafide.

30. The method of claim 1, wherein said inhibitor comprises an epipodophyllotoxin.

31. The method of claim 26, wherein said inhibitor comprises an antracededione.

32. The method of claim 1, wherein said inhibitor comprises merbarone.

33. The method of claim 1, wherein said inhibitor comprises teniposide.

34. The method of claim 1, wherein said inhibitor comprises indole-4,7-quinone.

35. The method of claim 1, wherein said inhibitor comprises elenic acid.

36. The method of claim 1, wherein said inhibitor comprises a 1-cyclopropyl-6,8-difluoro-1,4-dihyro-7-(2,6-dimethyl-4-pyridinyl)-4-substituted quinoline.

37. The method of claim 1, wherein said inhibitor comprises a 3-benzylquinoline.

38. The method of claim 1, wherein said inhibitor inhibits DNA topoisomerase I.

39. The method of claim 1, wherein said inhibitor inhibits DNA topoisomerase II.

40. The method of claim 1, wherein said inhibitor inhibits said DNA topoisomerase by interacting directly with the active site on said DNA topoisomerase.

41. The method of claim 1, wherein said inhibitor inhibits DNA topoisomerase by preventing the binding of ATP to said DNA topoisomerase.

42. The method of claim 1, wherein said inhibitor inhibits DNA topoisomerase by stabilization of the complex formed between DNA and said DNA topoisomerase during the action of said DNA topoisomerase.

43. The method of claim 1, wherein the concentration of said inhibitor of in said composition is between 0.1% and 30%.

44. The method of claim 1, wherein the composition provides a reduction in hair growth of at least 30% when tested in the Golden Syrian hamster assay.

45. The method of claim 1, wherein the composition provides a reduction in hair growth of at least 50% when tested in the Golden Syrian hamster assay.

46. The method of claim 1, wherein the composition provides a reduction in hair growth of at least 60% when tested in the Golden Syrian hamster assay.

47. The method of claim 1, wherein the inhibitor is applied to the skin in an amount of from 10 to 3000 micrograms of said inhibitor per square centimeter of skin.

48. The method of claim 47, wherein said mammal is a human.

49. The method of claim 47, wherein said area of skin is on the face of the human.

50. The method of claim 47, wherein said area of skin is on a leg of the human.

51. The method of claim 47, wherein said area of skin is on an arm of the human.

52. The method of claim 47, wherein said area of skin is in an armpit of the human.

53. The method of claim 47, wherein said area of skin in on the torso of the human.

54. The method of claim 47, wherein said human is a woman suffering from hirsutism.

55. A method of reducing mammalian hair growth which comprises
- selecting an area of skin from which reduced hair growth in desired; and
- inhibiting DNA topoisomerase in said area of skin sufficiently to cause a reduction in hair growth in said area of skin.

* * * * *